US008945222B2

(12) United States Patent
Linares

(10) Patent No.: US 8,945,222 B2
(45) Date of Patent: Feb. 3, 2015

(54) WEAR COMPENSATING JOINT ASSEMBLY INCORPORATING A PRESSURIZED FLUID INJECTABLE RESERVOIR UPWARDLY BIASING A HARDENED PLASTIC WITH A WEAR SURFACE

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 835 days.

(21) Appl. No.: 12/408,143

(22) Filed: Mar. 20, 2009

(65) Prior Publication Data

US 2010/0241234 A1    Sep. 23, 2010

(51) Int. Cl.
*A61F 2/28* (2006.01)
*A61F 2/30* (2006.01)
*A61F 2/38* (2006.01)
*A61L 27/50* (2006.01)
*A61F 2/48* (2006.01)

(52) U.S. Cl.
CPC ... *A61F 2/30* (2013.01); *A61F 2/38* (2013.01); *A61L 27/502* (2013.01); *A61F 2002/30523* (2013.01); *A61F 2002/3055* (2013.01); *A61F 2002/30563* (2013.01); *A61F 2002/30566* (2013.01); *A61F 2002/30581* (2013.01); *A61F 2002/30583* (2013.01); *A61F 2002/30584* (2013.01); *A61F 2002/30601* (2013.01); *A61F 2002/485* (2013.01); *A61F 2210/0085* (2013.01); *A61F 2220/0025* (2013.01); *A61L 2430/24* (2013.01)
USPC ..................................... 623/17.11; 623/18.11

(58) Field of Classification Search
CPC ............. A61F 2/30; A61F 2/38; A61F 2/441;
A61F 2002/30581; A61F 2002/30583; A61F 2002/501; A61F 2002/5015; A61F 2002/5032; A61F 2002/74; A61F 2250/0003
USPC .......... 623/18.11, 19.11, 20.14, 17.12, 22.13, 623/37, 56
See application file for complete search history.

(56) References Cited

U.S. PATENT DOCUMENTS

| | | | |
|---|---|---|---|
| 4,170,794 A | 10/1979 | Zeibig et al. | |
| 4,431,328 A | 2/1984 | Smith | |
| 4,908,034 A | 3/1990 | Weightman et al. | |
| 5,071,435 A * | 12/1991 | Fuchs et al. | 623/23.47 |
| 5,197,987 A | 3/1993 | Koch et al. | |
| 5,358,525 A | 10/1994 | Fox et al. | |

(Continued)

FOREIGN PATENT DOCUMENTS

| | | | |
|---|---|---|---|
| JP | 01249049 A | 10/1989 | |
| WO | WO-9625127 A1 | 8/1996 | |

*Primary Examiner* — Christopher D Prone
(74) *Attorney, Agent, or Firm* — Gifford, Krass, Sprinkle, Anderson & Citkowski, P.C.; Douglas J. McEvoy

(57) ABSTRACT

An artificial joint associated with an implant having a pair of three dimensional and structurally extending bones, each defining a contoured and opposing end face, which collectively defines a joint location. At least one plasticized and three dimensional shaped disk, such as a hardened and sanitary plastic material, is seated within a selected end cavity associated with a first of the bones. The disk exhibits an exterior surface configuration mating with an opposing end face of the other bone and which is biased, such as by a pressurized and fluid-filled bladder seated against an underside of the disc, in a contacting fashion against the other bone to establish a continuous wear surface.

3 Claims, 5 Drawing Sheets

(56) References Cited

U.S. PATENT DOCUMENTS

| | | |
|---|---|---|
| 5,662,158 A | 9/1997 | Caldarise |
| 5,735,905 A * | 4/1998 | Parr .................... 623/23.11 |
| 6,008,432 A | 12/1999 | Taylor |
| 6,187,045 B1 | 2/2001 | Fehring et al. |
| 6,217,617 B1 * | 4/2001 | Bonutti .................... 623/20.14 |
| 6,248,131 B1 * | 6/2001 | Felt et al. ................ 623/17.12 |
| 6,258,126 B1 | 7/2001 | Colleran |
| 6,344,059 B1 * | 2/2002 | Krakovits et al. .......... 623/20.31 |
| 6,414,086 B1 | 7/2002 | Wang et al. |
| 6,539,607 B1 | 4/2003 | Fehring et al. |
| 6,645,251 B2 | 11/2003 | Salehi et al. |
| 6,695,884 B1 | 2/2004 | Townley |
| 6,773,520 B1 | 8/2004 | Fehring et al. |
| 6,797,007 B1 | 9/2004 | Von Chamier et al. |
| 6,869,448 B2 | 3/2005 | Tuke et al. |
| 7,326,252 B2 | 2/2008 | Otto et al. |
| 7,338,529 B1 | 3/2008 | Higgins |
| 7,422,605 B2 | 9/2008 | Burstein et al. |
| 2002/0022889 A1 * | 2/2002 | Chibrac et al. .............. 623/18.11 |
| 2005/0171604 A1 | 8/2005 | Michalow |
| 2006/0241766 A1 | 10/2006 | Felton et al. |
| 2009/0076605 A1 * | 3/2009 | Linares .................... 623/14.12 |

* cited by examiner

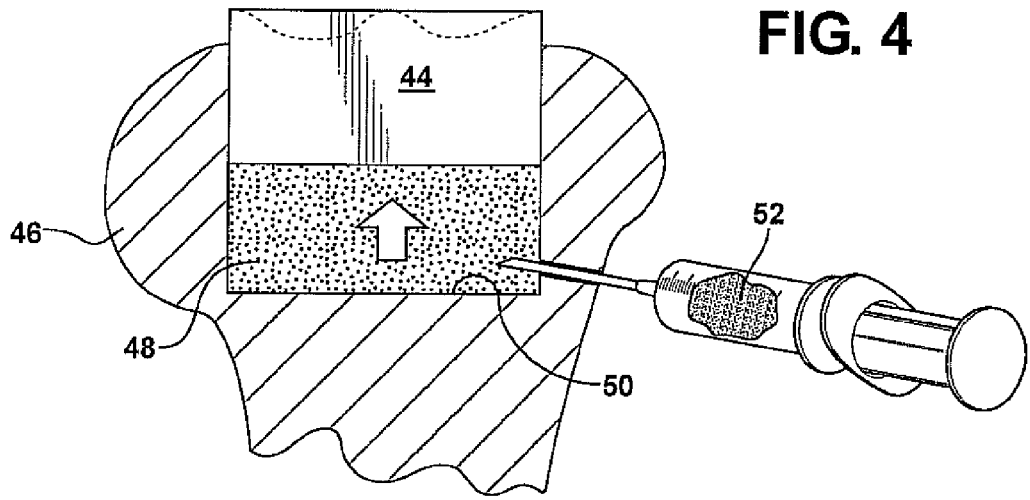
FIG. 4
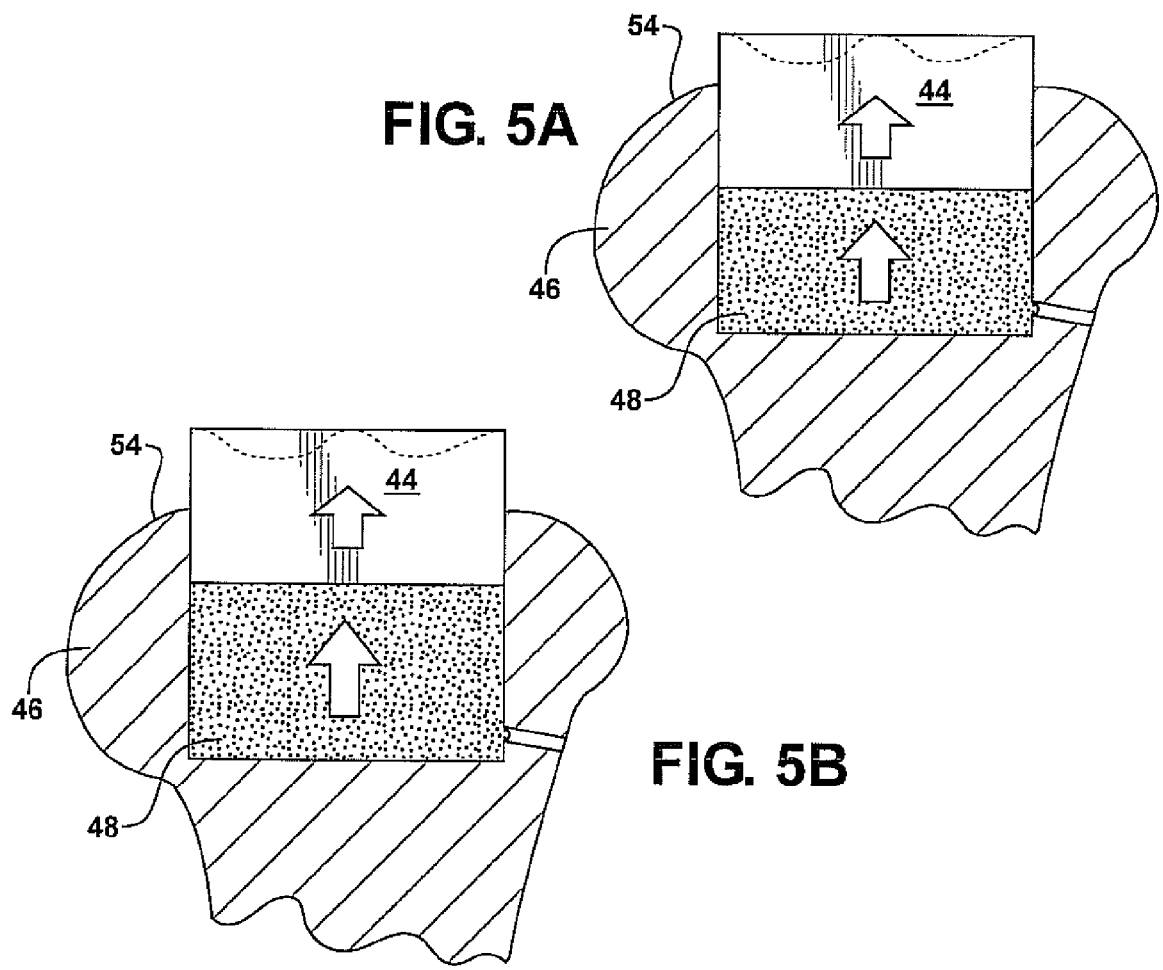
FIG. 5A
FIG. 5B

WEAR COMPENSATING JOINT ASSEMBLY INCORPORATING A PRESSURIZED FLUID INJECTABLE RESERVOIR UPWARDLY BIASING A HARDENED PLASTIC WITH A WEAR SURFACE

FIELD OF THE INVENTION

The present invention is an artificial implant for use with either real or artificial human bones. In particular, the implant of the present invention is an improvement over prior art implants, typically those constructed of a metallic or other synthetic material, in that it provides ballasting and substantially frictionless support to opposing ends of first and second bones associated with the joint. In a preferred application, a ballasting fluid, such as contained within a bladder, establishes a displacing pressure against an underside of a wear disk displaceably mounted to the selected joint bone, and in order to provide a continuously contacting wear surface. Additional variants disclose other mechanisms for biasing the wear disc in the desired manner for incrementally advancing the wear disk against the joint zone in order to provide a long-term and continuous wear surface associated with the implant application.

BACKGROUND OF THE INVENTION

The prior art is well documented with examples of prosthetic implant devices, such as particular useful as replacement joints. The objective of such devices is to replicate, to the degree possible, the normal functionality of a user's joint while providing for a degree of ongoing effectiveness and durability.

A problem associated with prior art artificial joint implants is the eventual wearing away of either or both of the abrading wear surfaces associated with the prosthetic joint implants. This problem is often compounded in situations where a normal (remaining) bone end surface defines a first half of a joint assembly, this arrayed opposite a prosthetic installed artificial wear surface, such as defining a part of an artificial implant bone or alternatively fashioned to a worn end of an opposite existing bone, and such that first and second different materials with different wear properties result.

Noteworthy examples of joint constructions drawn from the prior art include the bone joint endo-prosthesis of Zeibeg et al., U.S. Pat. No. 4,170,794, and which includes a spherical body interiorly apertured to receive a shaft spigot. A spreader includes a material which, upon wetted, swells. The material is wrapped over the spigot such that radial expansion provides shaping or profiling of the spreader for effective retention in a joint zone.

A non-medical example of a ball and joint socket is disclosed in Smith, U.S. Pat. No. 4,431,328, and which teaches an enlarged diameter half ball member disposed in a socket member and having a recess in which is engaged a biasing insert member made of a resilient or elastomeric material placed under compression during assembly of the joint. The joint bearing surfaces are elastically pre-loaded in an appropriate direction which causes firm engagement of the bearing surfaces in mutual engagement, preventing play and rattle of the joint and compensating for wear.

Additional examples of knee joint wear reducing implants include the prosthesis shown in Koch et al., U.S. Pat. No. 5,197,987 in which a tibia metal plate and a femur attached portion sandwich there-between an intermediate plastic part. Support members of hard material are distributed in the bearing surface of the intermediate plastic part, such as to receive the femur part thereon. The bearing surfaces of the support members are integrated in the bearing surface of the intermediate part and are provided with dual surfaces to receive different bearing surfaces of the femur part, each of which can exhibit a different radius of curvature.

Other noteworthy examples of implant assemblies drawn from the prior art include the artificial implant of Salehi et al., U.S. Pat. No. 6,645,251, this exhibiting reduced wear areas in the form of indentations, grooves, dimples, patterns, holes channels and slots.

SUMMARY OF TEE INVENTION

The present invention discloses an artificial joint, such as associated with an implant, and which is an improvement over the prior art in that it maintains continuous wear between opposing and joint defining surfaces. The joint includes a pair of three dimensional and structurally extending bones, such as each including any of a natural bone or a plasticized and/or metallic material, and each further defining a contoured and opposing end face, which collectively defines a joint location.

At least one plasticized and three dimensional shaped disk, such as a hardened and sanitary plastic material, is seated within a selected end cavity associated with a first of the bones. The disk exhibits an exterior surface configuration mating with an opposing end face of the other bone and which is biased, such as by a pressurized and fluid-filled bladder seated against an underside of the disc, in a contacting fashion against the other bone to establish a continuous wear surface. A needle can be employed for inserting the fluid material within the bladder or, alternatively, a nipple and extending line can be incorporated into the bone for introducing any type of fluidic, this including also pneumatic pressurized air, into the bladder.

A curable/settable fluidic material can be injected in the bladder and may further include such as at least one of an epoxy, a urethane, a gelatin and a two-part hardener. Other options for biasing the three dimensional wear disk include the provision of an upward biasing spring or even a mechanical linkage for actuating a threadably engaged plug located underneath the disk and within a base of an associated and first bone defined cavity. In the instance of a linkage, a rotation to linear displacement of the plug causes the disk to be progressively elevated against an opposing surface of the second bone end, this again in response to continual wear-away of a surface of the disk.

BRIEF DESCRIPTION OF THE DRAWINGS

Reference will now be made to the attached drawings, when read in combination with the following detailed description, wherein like reference numerals refer to like parts throughout the several views, and in which:

FIG. 4 an illustration of a further variant of the wear disk assembly and including a pressure injectable fluid within an underside located ballasting bladder in contact with the upwardly displaceable wear disk;

FIG. 5A is an enlarged illustration of the wear disk in FIG. 4 in a first pre-displaced configuration relative to the bone end face within which it is seatingly mounted;

FIG. 5B is a successive illustration of the wear disk in a substantially upwardly displaced position due to the underside biasing forces of the ballasting fluid;

DETAILED DESCRIPTION OF THE PREFERRED EMBODIMENTS

Figure 1:
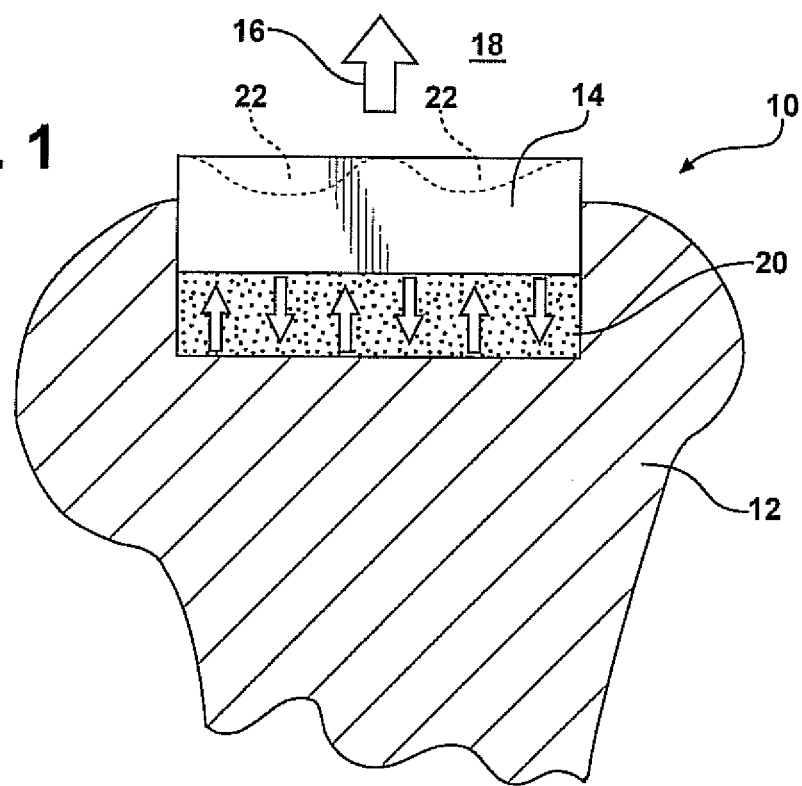
FIG. 1 is a side cutaway illustration of an artificial knee implant and illustrating a selected bone with underside fluid pressure biasing and linearly displaceable/surface mounted wear disk according to a selected embodiment of the present inventions.

Referring now to FIG. 1, a first embodiment is illustrated at 10 of an artificial knee/joint implant according to the present inventions. As previously described, the skeletal implant is intended to operate in one variant as a replacement for human bone and joint structure (such as resulting from disease, accidents, etc.) and which is further an improvement over existing prosthetic metal implants and the like. As further described herein, modifications of the joint design are also envisioned, and such as which can include an existing bone with (substantially undamaged) end face employed in combination with a prosthetic insert with incorporated three dimensional and progressively biased wear element.

Referring first to FIG. 1, a side cutaway illustration is shown of a first selected bone 12 of the artificial knee implant, a corresponding and opposing bone not being shown and which collectively defines a joint structure with associated ligaments. The bones are typically artificial prostheses, these including such as plastic, metal or other suitable material constructions which exhibit the necessary properties of durability and resilience, it again being understood from the foregoing discussion that a suitable existing or reconfigured natural bone can also be employed in a joint assembly, and such as further which may include an opposing artificial implanted bone such as shown at 12.

The bones each further have a specified shape and size and establish a joint selected from a group including at least one of upper/lower knee joint and an outer/inner ball and socket joint. Additional variants of the invention also contemplate the ability to retrofit an existing human bone, such as through the adaptation of unique medical drill and installation techniques, and in order to install a progressive wearing component into the joint defined region.

A common aspect of the invention, associated with each of the disclosed embodiments, is the ability to linearly displace such as a hardened and sanitary plastic disk 14 in a direction as referenced by linear directional arrow 16, and in a direction towards an opposing bone (not shown) within a general joint region 18. The ability to apply a continuous underside pressure to the (hardened) plastic disk 14 results in longer term wear characteristics and concurrent decrease of the likelihood of the patient having to undergo implant replacement surgery until many years have passed from an initial implant surgery.

The disk 14 is further capable of being generally seated in linearly displaceable fashion within the associated machined or in-molded end face of the bone and, in use, win not unseat from the bone due to the opposing established nature of a further joint defining bone (not shown) with associated ligaments. The term disk as used herein in reference to element 14 is further understood to envision and include and encompass any three dimensionally configured wear element, this including also spherical, elliptical cylindrical, three dimensional polygonal, as well as any other modifiable shape or configuration and which can be suitably incorporated into a joint assembly such as represented by selected bone 12 in FIG. 1 (or any other potential joint defining bone which may be otherwise configured).

Unique to the embodiment of FIG. 1, is the installation of an underside rubberized or other biasingly deflecting component, such as an elastic rubber layer 20. The layer 20, while incorporating a rubberized material in one non-limiting application, is also understood to include the provision of any other form of upwardly biasing technology, this as will be subsequently described also potentially including spring biasing, mechanical linkage and fluid bladder biasing technology. That said, the rubberized layer 20 illustrated encompasses one possible example of a relatively minimal bias inducing substrate material in use with the three dimensional shaped wear element 14.

The upward biasing of the 3D wear element (illustrated again by disk 14) assists in maintaining such as a plastic to metal (or other material) contact to compensate for ongoing wear to an intentionally long-term wear absorbing component. A feature of the invention is to enable the sacrificial disk 14 to wear away over a long period of time, while still maintaining the desired joint defining pressure and due to the underside force application established by the selected upwardly biasing component. Although not clearly illustrated in the cutaway view of FIG. 1, the disk 14 can exhibit an ergonomically configured upper surface, see depressions 22, and which creates such as seating locations for receiving opposing end face projecting locations of an opposing bone (not shown), the additional bone such as held in place by suitable ligaments or the like in order to create a desired joint defined wear zone.

Figure 2:
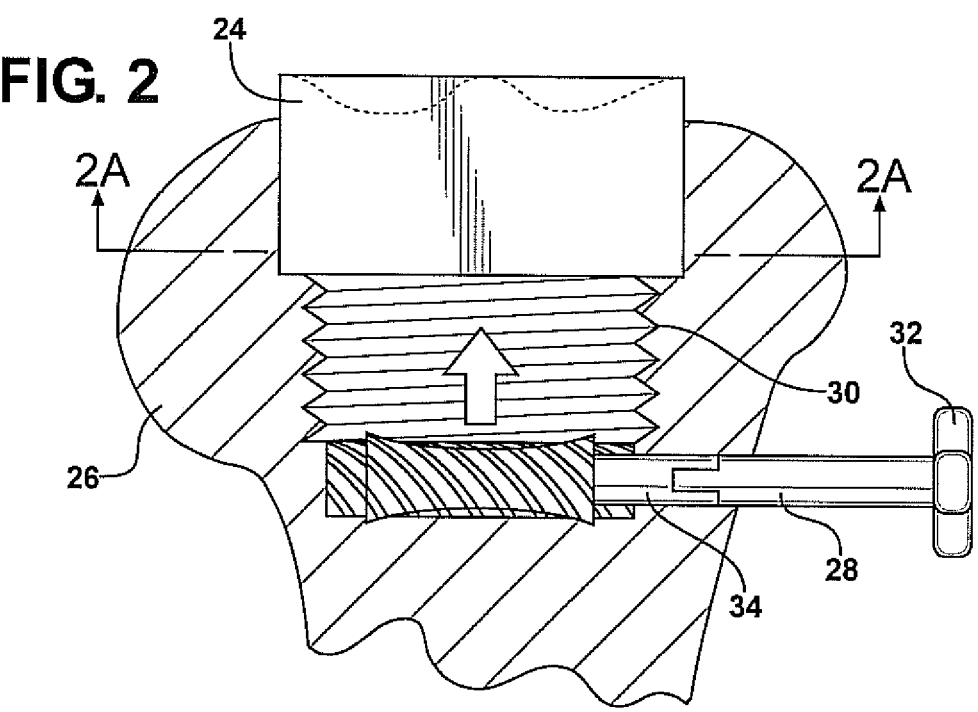
FIG. 2 is a side cutaway illustration of another version of displaceably biased wear disk and including a first version of mechanical linkage for upwardly biasing the wear disk against an opposing bone surface (not shown)

Referring now to FIG. 2, a side cutaway illustration is shown of another version of displaceably biased wear disk 24, this being seated (or contained) within an associated bone 26 and including a first version of mechanical linkage 28 for upwardly biasing the wear disk 24 against an opposing bone surface (not shown). The linkage arrangement of FIG. 2 can include a threadably installed and upwardly displaceable plug 30, this being rotated in a selected direction by such as a turn wheel 32 or other linkage connection located outside of the joint zone and in order to upwardly displace the wear disk 24 in the desired direction for creating a continuously biased joint zone. Although not shown, an appropriate slip ring or other component can be introduced between the plug 30 and the three dimensional biased component (e.g. again disk 24)

and in order to the prevent the disk 24 from rotating as it is upwardly biased in response to the rotational to linear displacement of the plug 30.

Additional to a first linkage component, again at 28, a secondary and interengaging component 34 can be retained within the body of the bone 26 (such as again an artificial material within which the various components are in-molded or otherwise manufactured) and in turn causing the threadable plug 30 and associated disk to be upwardly displaced in a constant wear compensating fashion to maintain the in contact within the opposing joint bone. The linkage components can further incorporate any of a bevel gear arrangement or other like linkage, and in order to establish a desired and reliable degree of mechanical action with a minimum of space requirements within the bone.

Figure 2A:
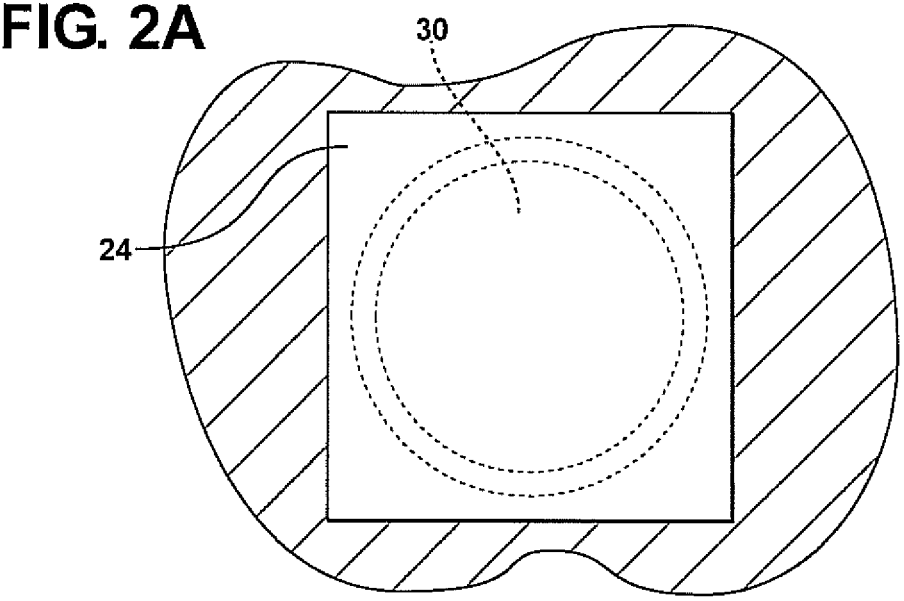
FIG. 2A is an end cutaway view taken along line 2A-2A of the selected mounting disc arrangement of FIG. 2.

FIG. 2A is a cutaway end view taken along line 2A-2A of FIG. 2 of a selected mounting disc arrangement and such as showing the disk 24 with underside located and threaded rotatable plug 30. As referenced in combination with FIG. 2, inter-engaging sets of threads are formed in both the exterior side of the plug 30 (such as which can be a plastic or lightweight metal) and the corresponding inner annular wall of the bone 26, this being pre-drilled or other molded in the desired shape (such as also through the application of a ½ mold process for creating identical halves of a bone, and which are then assembled together by such as sintering operation or, alternatively, by sonic welding techniques.

Figure 3:
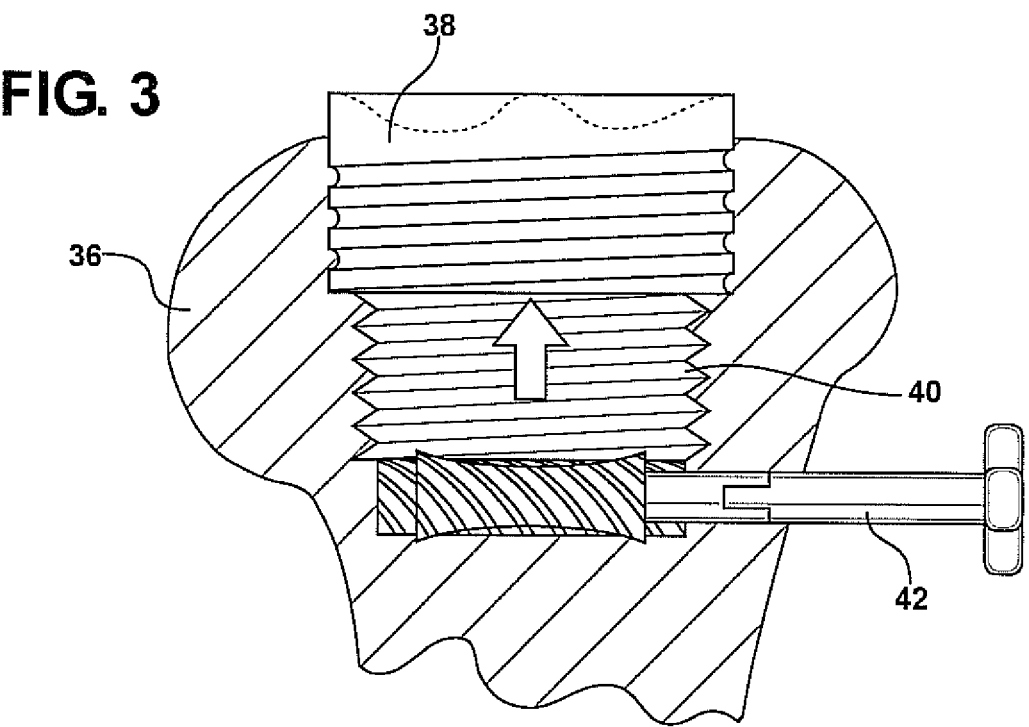
FIG. 3 is an illustration similar to FIG. 2 of an other related version of mechanically elevate-able linkage associated with a wear disk assembly.

As shown in FIG. 3, an illustration similar to FIG. 2 is provided of an other related version of mechanically elevateable linkage associated with a wear disk assembly and which includes a bone 36 within which is seated a polypropylene or other plastic constructed disk 38. Another version of threadably rotatable/linearly displaceable plug is also shown at 40 and, upon actuation of the associated mechanical linkage 42, results in the hardened plastic (sacrificial) disk 38 being iteratively raised in order to maintain contact with the opposing joint surface, and again to accommodate progressive wear of the disk 38 over time.

FIG. 4 is an illustration of a further variant of the wear disk assembly 44 associated with an artificial bone 46 and incorporating a pressure injectable fluid 48 within an underside located ballasting bladder 50, the bladder in turn being in contact with the upwardly displaceable wear disk 44. A needle 52 (or other suitable fluid injection mechanism) is provided for injecting a specified volume of the ballasting fluid 48 (this including such as a water-based or other synthetically derived fluid-based composition) and which operates to upwardly displace the progressive wear disk 44 to a desired pressure applied and seating configuration with au opposing joint defining bone.

The fluid can again include such as a epoxy/urethane/gelatin and which may also incorporate a two part hardener in order to cure and harden the mixture upon insertion and upon formation of the bladder to the desired supporting shape. The ballasting bladder 48 is further defined by such as a fluid retaining and flexible/stretchable body including a plasticized or other suitable artificial material. Although not further shown in either this or the succeeding embodiments, it is further understood that a suitable ligament structure is employed for retaining the bones and resultant joint created therebetween in a desired relative positioning.

Referring now to FIG. 5A, an enlarged illustration of the wear disk 44 in FIG. 4 is illustrated in a first pre-displaced configuration relative to a top end face 54 of the bone 46, and within which the hardened plastic wear disk 44 is seatingly mounted. FIG. 5B is a successive illustration of the wear disk 44 in a substantially upwardly displaced position (relative again to the end surface 54 of the associated bone) and due to the underside biasing forces exerted by the ballasting fluid 48.

Figure 6:
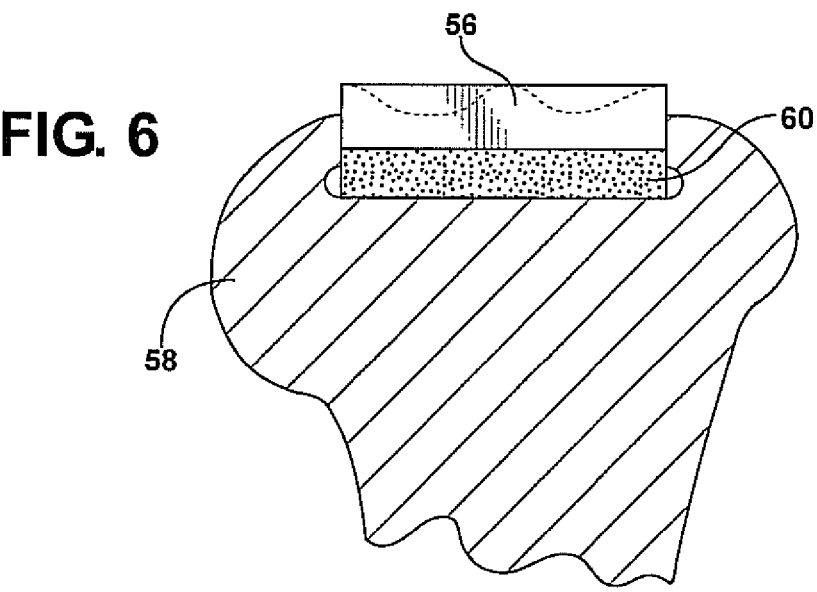
FIG. 6 is an alternate variant and in which a hard plastic wear disk is biasingly supported upon an enclosed and rubberized member within the artificial bone according to the present inventions.
Figures 7A, 7B:
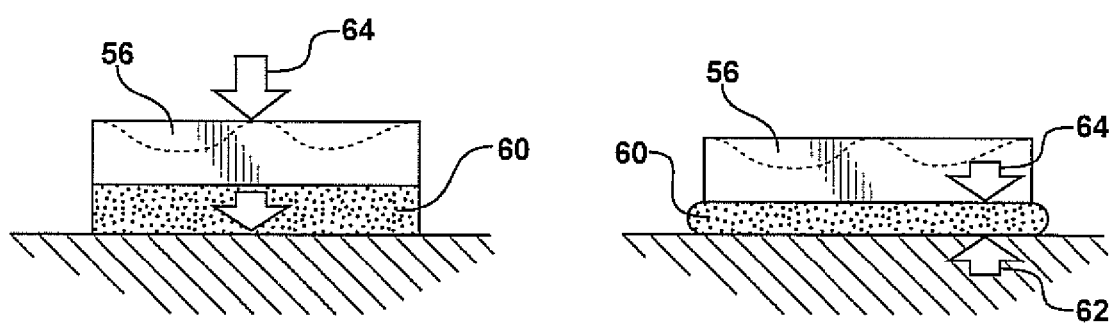
FIG. 7A is an enlarged illustration of the wear disk and underside rubberized component in FIG. 6 in a first and initially/inwardly deflecting condition resulting from biasing forces applied by an opposing and joint zone defining bone.
FIG. 7B is a successive illustration of the wear disk in FIG. 7A being biased in a reversed direction as a result of recoil forces generated by the underside located rubber component.

FIG. 6 is an alternate variant in which a hard plastic wear disk 56 is biasingly supported in an end-seating and upwardly biased fashion upon a bone 58, further such as by an enclosed and rubberized member 60. FIG. 7A is an enlarged illustration of the wear disk 56 and underside rubberized component 60 in FIG. 6, and in a first and initially/inwardly deflecting condition resulting from biasing forces applied by an opposing and joint zone defining bone 58. FIG. 7B is a successive illustration of the wear disk 56 in FIG. 7A being biased in a reversed direction, see arrow 62, as a result of recoil forces generated by the underside located rubber component 60 against the downwardly exerting forces (at 64) applied by an opposing and joint establishing bone.

Figure 8:
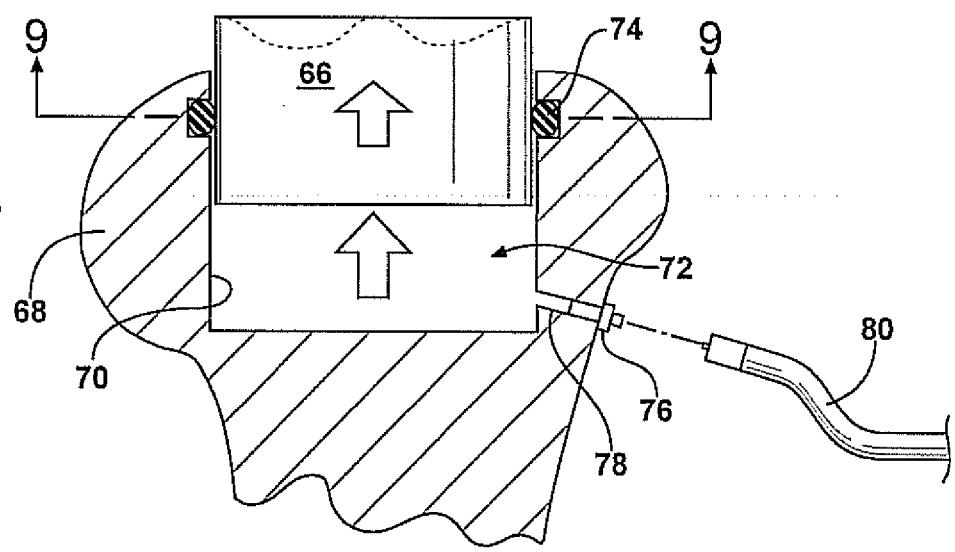
FIG. 8 is a side cutaway illustration of another variation of a pneumatic air pressure displaced wear disk incorporated into a bone and further including a surrounding O-ring seal.

FIG. 8 is a side cutaway illustration of another variation of a pneumatic air pressure displaced wear disk 66 incorporated into a bone 68. Similar to the embodiment of FIG. 4, a flexible and fluid retaining bladder or the like, at 70, can be provided and which is seated inside of interior pocket established within the end recessed configuration of the bone 68, and such as which receives a volume of a pressurized air 72.

Figure 9:
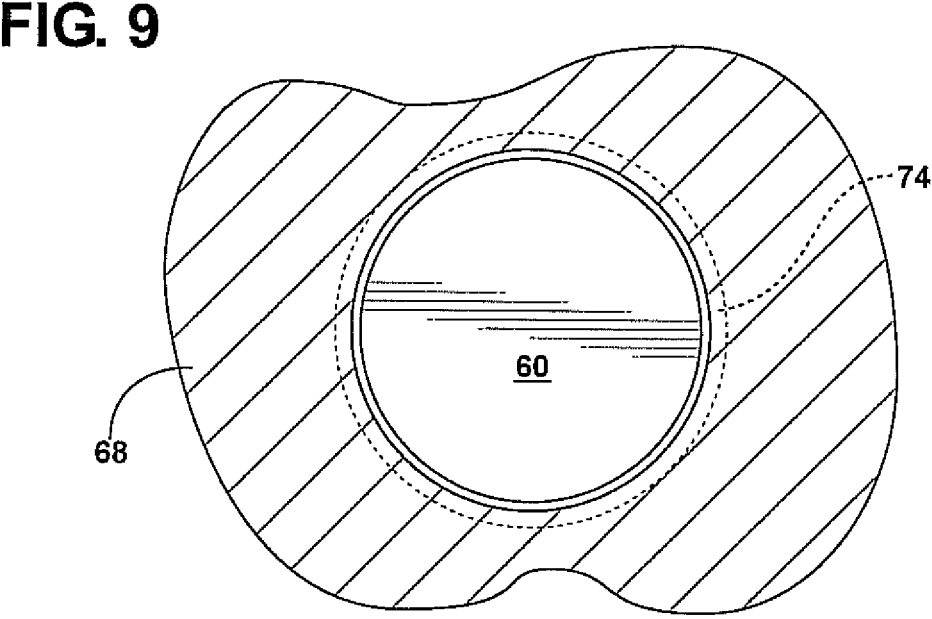
FIG. 9 a cutaway view taken along line A-A of FIG. 8 and illustrating the concentric arrangement of wear disk and O-ring seal.

An O-ring seal 74 is seated annularly and in contacting fashion about an outer circumference of the wear disk 66 and operates to prevent fluid pressure from leaking about the outer edges of the disk 66 (and in an instance such as where the associated bladder 70 may have incurred a leak). The O-ring seal 74 is further typically recessed mounted into an annular channel configuration defined within the surrounding interior wall of the bone 68 and provides the dual function of facilitating easy linear displacement of the disk 66. FIG. 9 is cutaway view taken along line A-A of FIG. 8 and further illustrating the concentric arrangement of wear disk 66 and O-ring seal 74 within the bone 68.

A nipple 76 can be configured upon a surface of the bone 68 and which can further include an interior passageway 78 (such as provided by an inner fluid line in-molded or otherwise produced with the bone 68. A pneumatic delivery hose 80 can attack such as to the nipple 76 located upon the bone, and in order to selectively re-pressurize or to adjust an existing interior seating pressure associated with the disk 66. Although not further specifically shown, any of the disclosed variants can further incorporate medically implanted sensors, and such as which can detect a biasing pressure applied by and against the wear disk 66, as well as additional joint integrity defining factors such as a degree of wear associated with the given disk and which can instruct when the disk may (eventually) require replacement.

Figure 10:
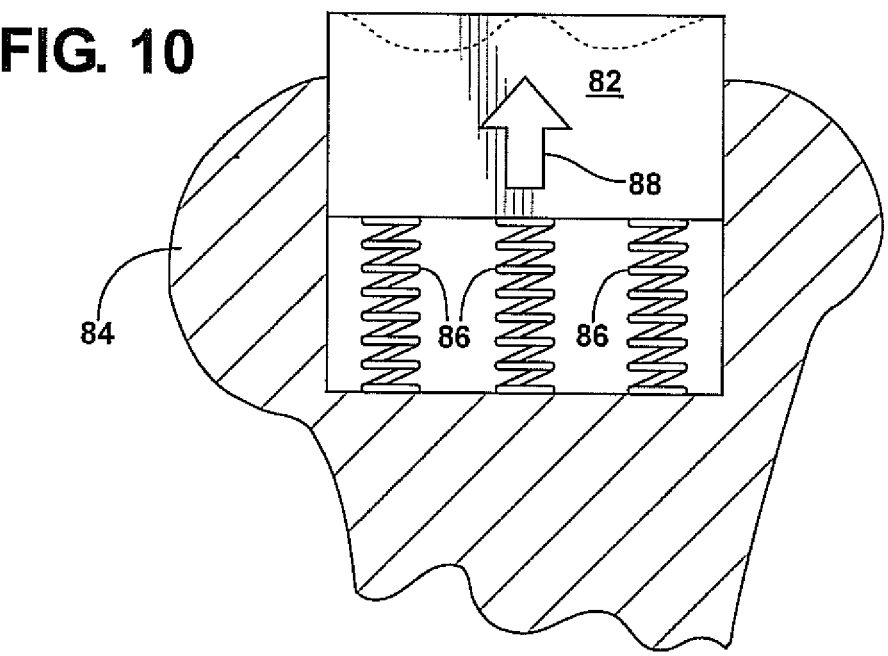
FIG. 10 is a further side cutaway view of a mechanical spring actuated wear disk for maintaining a consistent joint defined wear zone according to the present inventions.

Finally, and referring to FIG. 10, a further side cutaway view is shown of a mechanical spring actuated wear disk 82 for maintaining a consistent joint defined wear zone when seated in a corresponding and bone 84 defined end cavity. Illustrated at 86 are a plurality of springs, these seating within an underside base surface of the end cavity of the associated bone, as shown in FIG. 10, and providing the same dynamic characteristics as any of the preceding embodiments. Additional variants also envisioned a biasing force (see directional arrow 88) applied by the springs 86 and against the disk 82 modified through any appropriate mechanism Having described my invention, other and additional preferred embodiments will become apparent to those skilled in the art to which it pertains, without deviating from the scope of the appended claims.

I claim:

1. An implant kit adapted for use with a pair of joint defining bones, collectively defining a joint location, said kit comprising:

at least one of the joint defining bones including an artificial replacement bone exhibiting a contoured end face having an arcuate seating surface adapted to mate with an opposing surface of the other joint defining bone;

said artificial replacement bone further including a plasticized and three dimensional shaped disk having a substantial elliptical cylindrical cross section, said disk adapted to being seated within an end cavity configured within said artificial replacement bone and so that an outer circumference of said disk is in guided contact with an opposing side contact surface of the end cavity, said disk having a contoured and exposed end face which is congruent with said contoured end face of said artificial replacement bone and which is also capable of mating with the opposing end surface of the other joint defining bone;

a ballasting bladder pre-positioned within said end cavity in contact with an underside surface of said disk; and a fluid injection mechanism including a needle adapted to be inserted through an aperture in said artificial replacement bone, the aperture defining a passageway extending within said artificial replacement bone from an exterior location to an interior location in contact with said end cavity and said pre-positioned bladder such that said needle pierces said pre-positioned bladder, said pre-positioned bladder capable of being subsequently and repetitively filled by injection of a ballasting fluid introduced through said needle, in order to pressurize said pre-positioned bladder to elevate said disk by exerting a continuous upwardly displacing force against said disk, said outer circumference of said disk being maintained in contact against the other joint defining bone throughout its life in a continuously adjusted and pressure applied fashion, resulting from subsequent injections of additional volumes of said fluid, to compensate for continuous material loss resulting from abrading of said disk and to maintain a continuous wear surface between said disk and the other joint defining bone.

2. The implant kit as described in claim 1, said plasticized and three dimensional disk exhibiting a predetermined shape and size and further comprising a hardened and sanitary plastic material.

3. The implant kit as described in claim 1, said plasticized and three dimensional disk having a specified shape and size and establishing a joint selected from a group including at least one of upper/lower knee joint and an outer/inner ball and socket joint.

* * * * *